United States Patent [19]
Matsuoka

[11] Patent Number: 5,905,575
[45] Date of Patent: May 18, 1999

[54] SPHERICAL SURFACE INSPECTION EQUIPMENT FOR OPTICALLY EXAMINING THE SURFACE OF A SPHERE

[75] Inventor: Katsutoshi Matsuoka, Kanagawa, Japan

[73] Assignee: NSK Ltd., Tokyo, Japan

[21] Appl. No.: 08/845,469

[22] Filed: Apr. 25, 1997

[30] Foreign Application Priority Data

Apr. 25, 1996 [JP] Japan .................................. 8-127684
Mar. 31, 1997 [JP] Japan .................................. 9-94413

[51] Int. Cl.$^6$ ...................................................... G01B 9/02
[52] U.S. Cl. ............................................ 356/359; 356/360
[58] Field of Search ................................... 356/345, 359, 356/360

[56] References Cited

U.S. PATENT DOCUMENTS 5,327,220  7/1994  Erickson ................................ 356/359

*Primary Examiner*—Robert H. Kim
*Attorney, Agent, or Firm*—Sughrue, Mion, Zinn Macpeak & Seas, PLLC

[57] ABSTRACT

Spherical surface inspection equipment which optically examines the nature of the surface of a sphere to be examined, is made up of light illumination member including a point of light source for emitting a luminous flux, at predetermined angle of spread in a specific direction which is disposed in such a way that the exit point of the luminous flux matches a first focal point, and a curved-face mirror whose mirror surface is defined by a predetermined inner surface area which forms a part of a curved surface obtained by rotating a specific curve around a specific axis including the first focal point and includes and extends through at least 180 degrees around the axis. The spherical surface inspection equipment also includes sphere-to-be-examined drive member which retains the sphere such that its center is brought in alignment with the second focal point, and which rotates the sphere about the axis of rotation along a specific half of the meridian included between the poles on the surface of the sphere opposite to the predetermined inner surface of the curved-surface mirror; and surface nature determination member which limits the light reflected from the sphere to only the light reflected from an area corresponding to a predetermined width between the half of the specific meridian included between the poles and detects the thus-limited reflected light through use of at least one photodiode; and which determines the nature of the surface of the sphere according to the result of such detection.

6 Claims, 15 Drawing Sheets

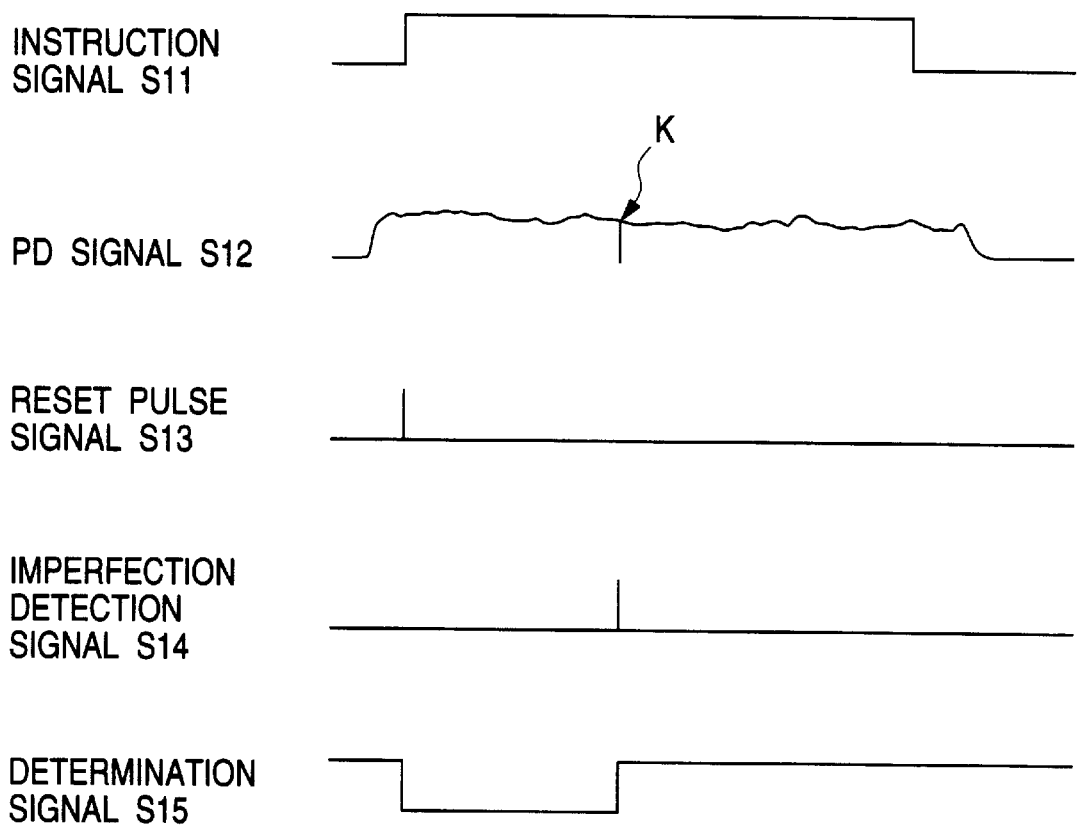

FROM SURFACE NATURE DETERMINATION MEMBER 8

FIG. 14A  CPA SIGNAL S22 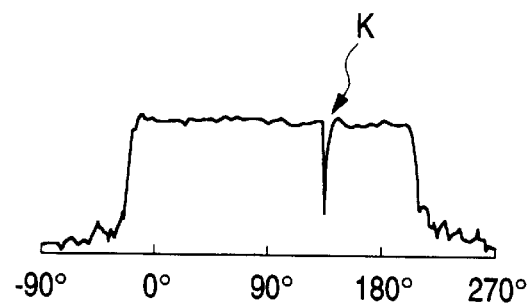
FIG. 14B  GATE SIGNAL S23 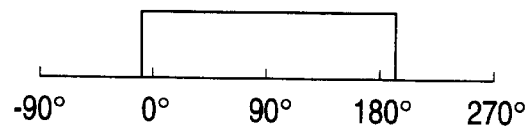
FIG. 14C  REFERENCE SIGNAL T 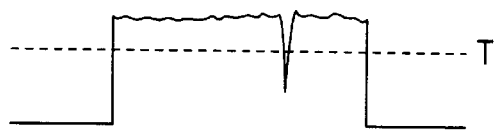
FIG. 14D  IMPERFECTION DETECTION SIGNAL S25 
→ TIME t
FIG. 15
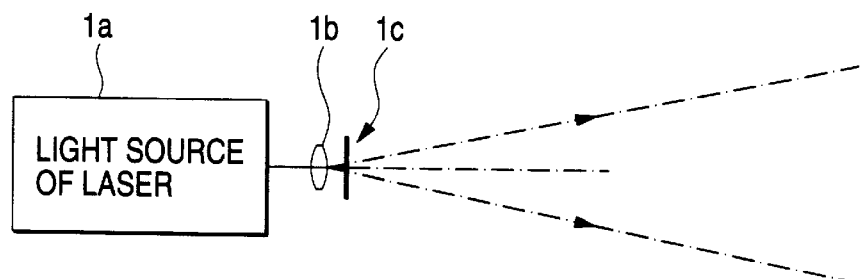

SPHERICAL SURFACE INSPECTION EQUIPMENT FOR OPTICALLY EXAMINING THE SURFACE OF A SPHERE

BACKGROUND OF THE INVENTION

The present invention relates to spherical surface inspection equipment for optically examining the surface nature of a sphere to be examined such as a steel ball.

1. Description of the Prior Art

As illustrated in FIG. 1, spherical surface inspection equipment having the following structure is already known as the previously described type of spherical surface inspection equipment. Specifically, the spherical surface inspection equipment is comprised of a semi-circumferential array 53 which includes a plurality of pairs of flood-light element 51 and light-receiving element 52 arranged in a semi-circumferential pattern at uniform angular intervals. The semi-circumferential array 53 is positioned in a circumferential direction of a steel ball 54 which is a ball to be examined. The steel ball 54 is rotated around a support axis 55 in the direction designated by arrow Y. The surface nature of the steel ball 54 is determined on the basis of an electrical signal output from the light-receiving element 52 (this spherical surface inspection equipment will be hereinafter referred to as a "first conventional example").

As illustrated in FIG. 2, in the first conventional example, the light emitted from the flood-light element 51 is reflected from the surface of the steel ball 54, and the thus-reflected light is received by the light-receiving element 52 disposed at a given angle alpha in relation to the flood-light element 51. The light-receiving element 52 converts the thus-received light into an electrical signal by a photoelectric converting element (not shown) such as a photo-diode. The thus-converted signal is output, via an amplifier and a gain control circuit (not shown). The level of the signal output from the light-receiving element 52 is compared with a given reference value, and the surface nature of the steel ball 54 is determined on the basis of the result of such comparison. In short, an examination is carried out as to whether or not there are imperfections such as flaws on the surface of the steel ball 54.

As illustrated in FIG. 3, there is another example of known spherical surface inspection equipment. The flood-light 56 (emitted from lighting equipment) incidents on the surface of the steel ball 54 which is rotating in the direction designated by arrow Z, and the light reflected from the surface of the steel ball 54 is collected into a point by use of a convex lens 57. An image of the thus-collected light is formed on a photoelectric converting element 58 such as a CCD (Charge-coupled Device). This example will be hereinafter referred to as a "second conventional example," and please refer to; e.g., Japanese Patent Unexamined Publication Nos. Sho-56-58643 and Sho-56-58644.

In the second conventional example, the photoelectric converting element 58 converts luminous energy into an electrical signal, and the nature of the spherical surface is determined on the basis of the level of the electrical signal. Specifically, a decision as to the presence or absence of imperfections in the steel ball 54 is performed on the basis of the level of the signal output from the photoelectric converting element 58. The second conventional example enables even the photoelectric converting element 58 having a small light-receiving area to examine the nature of the overall surface of the steel ball 54 by obliquely rotating at a given angle in relation to the steel ball 54.

However, in the first conventional example, it is necessary to examine the surface nature of the steel ball 54 with substantially identical sensitivity with regard to the diametrical dimension of the steel ball 54 (hereinafter referred to as the "size of the steel ball"). It is necessary to adjust the sensitivity of the spherical surface inspection equipment with regard to the detection of imperfections in the steel ball 54 every time the size of the steel ball changes. The allowable size of imperfections in a steel ball changes according to the size of the steel ball. In the case of the steel ball 54 having a small size, the allowable size of imperfections such as flaws must be set to a small size. In contrast, in the case of the steel ball 54 having a large size, the allowable size of imperfections may be set to a large size according to the size of the steel ball.

To prevent a decrease in the yield of steel balls, the sensitivity of the spherical surface inspection equipment is conventionally carried out according to the size of the steel ball so as to set the allowable size of imperfections corresponding to the size of the steel ball. For this reason, in the first conventional example, it is necessary to adjust and check the balancing of variations in the sensitivity of the photoelectric converting element to convert luminous energy into an electrical signal for each size of the steel ball.

In order to improve the capacity of the spherical surface inspection equipment to detect and resolve imperfections in view of surface nature, it is necessary to bring the light-receiving elements 52 as close to the vicinity of the steel ball 54 as possible such that the field of view of each light-receiving element 52 becomes narrow. For this reason, in the first conventional example, it is necessary to prepare the plurality of semi-circumferential arrays 53 tallying with the size of the steel ball beforehand. More specifically, in order to examine the nature of the surface of the steel ball 54 with high accuracy while the semi-circumferential array 53 is brought as close to the surface of the steel ball 54 as possible, it is necessary to manufacture a plurality of types of semi-circular arrays 53 having different pitch diameters according to the size of the steel ball. The spherical surface inspection equipment must be set by selection of a desired semi-circular array 53 corresponding to the size of the steel ball. It requires a lot of expense in time and effort to prepare for measurement.

In contrast, in the second conventional example, an image pick-up optical system determines a face-to-face distance of a steel ball to be examined (i.e., a first spacing "a" between the steel ball 54 and the lens 57 and a second spacing "b" between the convex lens 57 and the photoelectric converting element 58) and the magnification of an image (b/a). It is relatively easy to control in such a way that a relative distance; namely, the first spacing "a" and the second spacing "b," becomes constantly equal with respect to the steel ball 54 having a different size. However, it is difficult to ensure an image having uniform brightness by evenly illuminating the surface of the steel ball 54. More specifically, even when illumination light incidents on the surface of the steel ball 54, there is a great difference between the center of the illumination light and its periphery with regard to the angle at which the incoming light is reflected from the surface of the steel ball 54. It becomes difficult for the reflected light originated from the periphery of the illumination light to enter the lens 57, which in turn makes it impossible to produce an image having uniform brightness. The following method is conceivable. Specifically, as designated by a two-dot chain line in FIG. 3, a diffusing glass 59 is provided in the optical path of the illumination light, and the surface of the steel ball 54 is illuminated from many directions. The light reflected from the surface is diffused in various directions, and the diffuse reflections are collected into an image on the photoelectric conversion element 58.

However, if the diffusing glass 59 is disposed in the optical path, the illumination light is diffused in a wide range over the surface of the steel ball, thereby deteriorating the light-focusing efficiency of the convex lens 57. It is practically difficult to examine a wide range of the surface of the steel ball.

It is possible to change the capacity of the spherical surface inspection equipment to detect and resolve imperfections in terms of surface nature by changing the magnification of the optical system by use of the convex lens 57 according to the size of the steel ball. To obliquely rotate a steel ball, it is necessary to use a control roller manufactured according to the size of the steel ball and the degree of skew as disclosed in Japanese Patent Examined Publication (kokoku) Sho-42-17608, or it is necessary to provide the spherical surface inspection equipment with a skew mechanism as disclosed in Japanese Patent Unexamined Publication No. Sho-56-58643. Consequently, it is necessary to replace the previously-described component of the equipment each time the size of the steel ball changes. As in the first conventional example, it requires expense in time and effort to set the spherical surface inspection equipment. Further, the component is abraded or damaged as a result of contact between the component and the steel ball 54, thereby resulting in faulty oblique rotation of the steel ball. For this reason, in order to sufficiently ensure the result of inspection of the overall surface area of the steel ball 54, it is necessary for a person to carefully control the component. Furthermore, in practice, it is very difficult to manufacture a control roller and a skew mechanism capable of obliquely rotating the steel ball 54 having a diameter as small as 1 mm or thereabouts in view of production engineering. In short, as has been described above, the second conventional example has various problems with regard to production, as well as to the replacement and maintenance of a rotation control mechanism.

SUMMARY OF THE INVENTION

The present invention has been conceived in view of the aforementioned drawbacks in the prior art, and the object of the present invention is to provide spherical surface inspection equipment capable of easily examining the nature of the overall surface of a ball to be inspected; e.g., a steel ball, with high accuracy without changing an optical system according to the size of the steel ball.

To this end, the present invention provides Spherical surface inspection equipment for optically examining the nature of the surface of a sphere comprising:

a light illumination member including;

a point-source light for emitting a luminous flux at predetermined angle of spread in a specific direction which is disposed in such a way that the exit point of the luminous flux matches a first focal point; and a curved-surface mirror having a mirror surface defined by a predetermined inner surface area which forms a part of a curved surface obtained by rotating a specific curve around a specific axis containing the first focal point and extended through at least 180 degrees around the axis;

wherein the light illumination member is arranged such that the luminous flux emitted from the point-source light simultaneously enters an area including the predetermined inner surface area of the curved-surface mirror, and that the light reflected from the curved-surface mirror is focused on a second focal point contained in the specific axis;

sphere-to-be-examined driver for retaining the sphere such that its center is brought in alignment with the second focal point, and for rotating the sphere about a rotational axis defined by straightly connecting the two poles on the sphere, wherein a specific meridian extended through at least 180 degrees around the axis is defined on the surface of the sphere opposite to the predetermined inner surface of the curved-surface mirror by connecting the two poles along the surface of the sphere; and surface nature determination member for limiting the light reflected from the sphere to only the light reflected from an area corresponding to a predetermined width containing the specific meridian; for detecting the thus-limited reflected light with at least one photodiode; and for determining the nature of the surface of the sphere according to the result of such detection.

In the spherical surface inspection equipment of the present invention, the sphere-to-be-inspected drive member rotates the sphere around the predetermined axis that runs through the center of the sphere while retaining it in a predetermined position. The light illumination member deflects the light emitted from the light source toward the center of the sphere along at least area to be examined which is defined between the poles of the sphere in line with the predetermined axis. The luminous energy detection member guides the light reflected from the area of the sphere to be examined along a predetermined optical path and detects the luminous energy of the thus-guided light. The surface nature determination member determines the nature of the examined surface area of the sphere according to the thus-detected luminous energy. As a result, constant solid angle of the incoming light with respect to the sphere is ensured. It becomes unnecessary to adjust the solid angle of the incoming light with respect to the sphere by exchange of components so as to change an optical system according to variations in the size of the sphere. This saves labor involved in preparation for measurement, and the sphere can be examined while the optical axis of the incoming light is held stable.

The entire surface of the sphere is scanned by rotation of the sphere around the predetermined axis while the sphere is retained in the predetermined location. As a result, it becomes unnecessary to obliquely rotate the sphere, which in turn eliminates the need of a conventional control roller. Further, it becomes possible to eliminate the need of a skewing mechanism which may cause errors in the rotating speed, and the sphere can be examined while it rotates one time. Consequently, it is possible to provide inexpensive spherical surface inspection equipment capable of examining a small-sized sphere at a high speed with high accuracy, as well as of requiring easy operation and maintenance.

Moreover, the sphere does not need to be tilted, nor does it need to be scanned by light. Because, the incoming light simultaneously incidents on at least the area of the sphere through 180 degrees. Further, it is not necessary to ensure synchronization between the scanning of the area to be examined and the detection of the reflected light, which enables easy and reliable examination of the entire to circumference of the sphere.

BRIEF DESCRIPTION OF THE DRAWINGS

FIG. 5 is a timing chart illustrating signals input to and output from a surface nature determination member of the spherical surface inspection equipment illustrated in FIGS. 4A and 4B;

FIGS. 14A to 14D are representations of variations in the level of the principal signals of the surface nature determination member;

FIG. 15 is a diagrammatic representation of the principal elements of spherical surface inspection equipment according to a third embodiment of the present invention;

PREFERRED EMBODIMENTS OF THE INVENTION

With reference to the accompanying drawings, preferred embodiments of the present invention will be described hereinbelow.

(FIRST EMBODIMENT)

Figure 1:
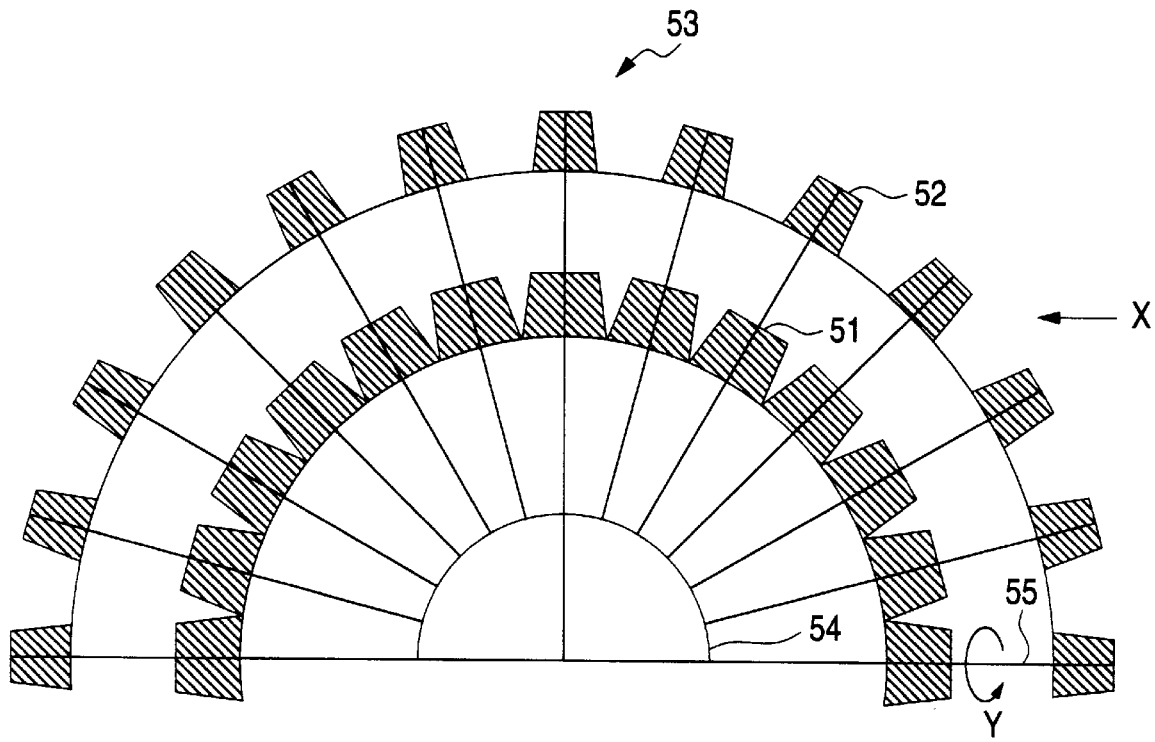
FIG. 1 is a schematic representation of the principal elements of a first example of conventional spherical surface inspection equipment.
Figure 2:
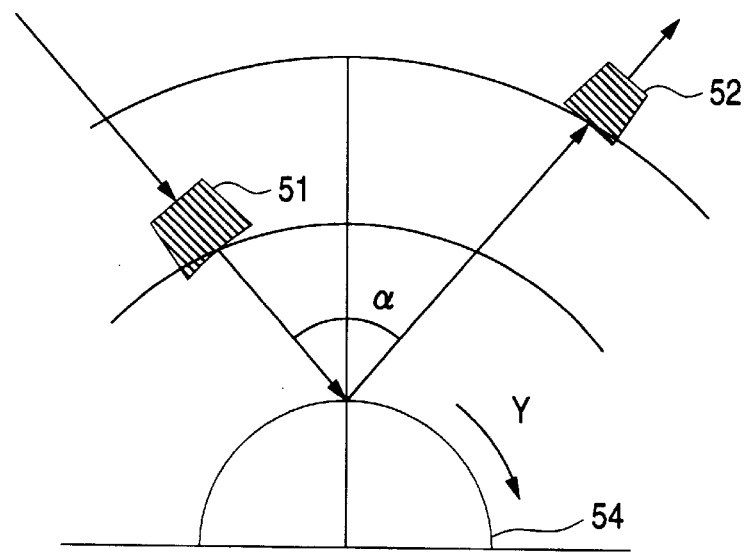
FIG. 2 is a schematic representation of the spherical surface inspection equipment as view in the direction designated by X in FIG. 1.
Figure 3:
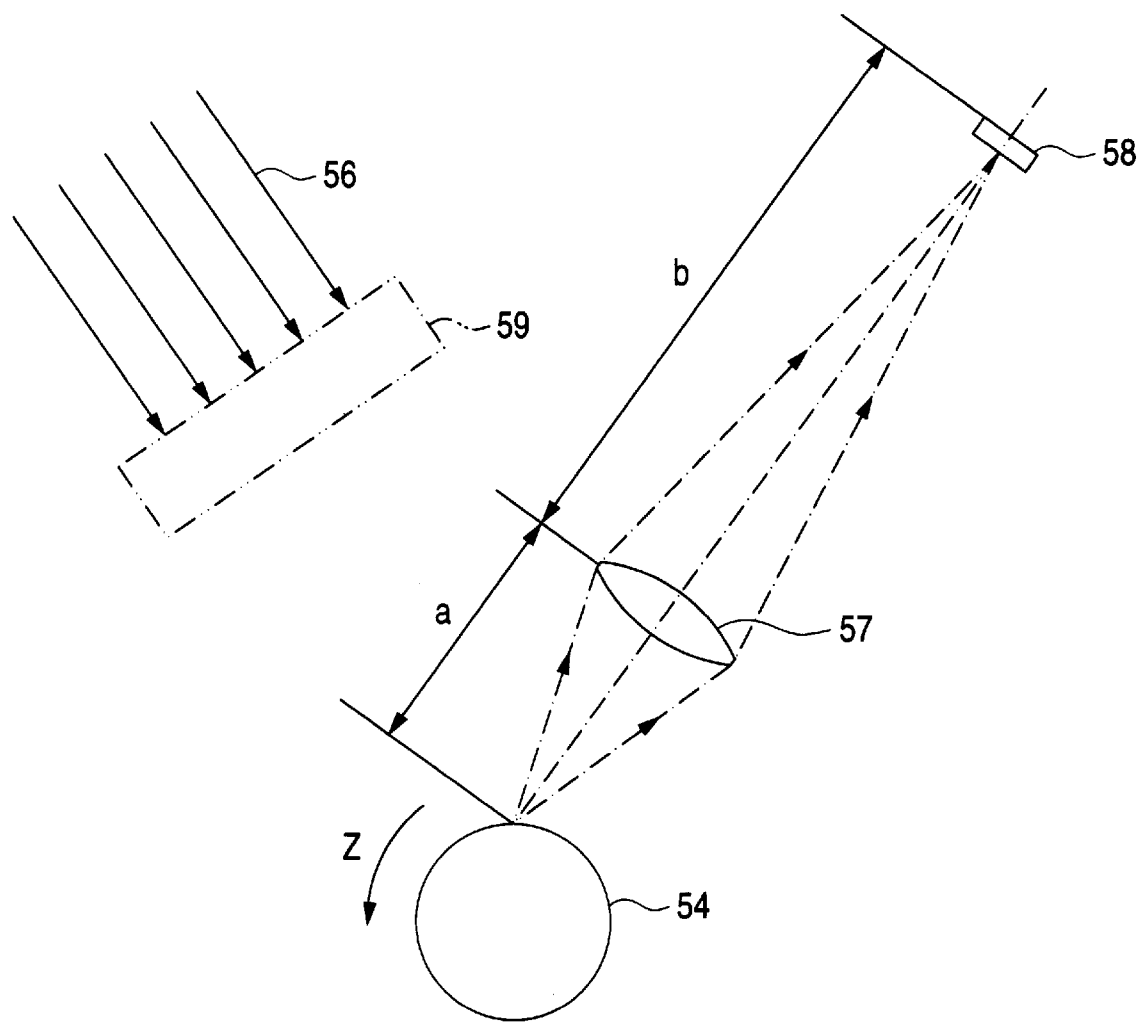
FIG. 3 is a schematic representation of the principal elements of a second example of the conventional spherical surface inspection equipment.
Figure 4A:
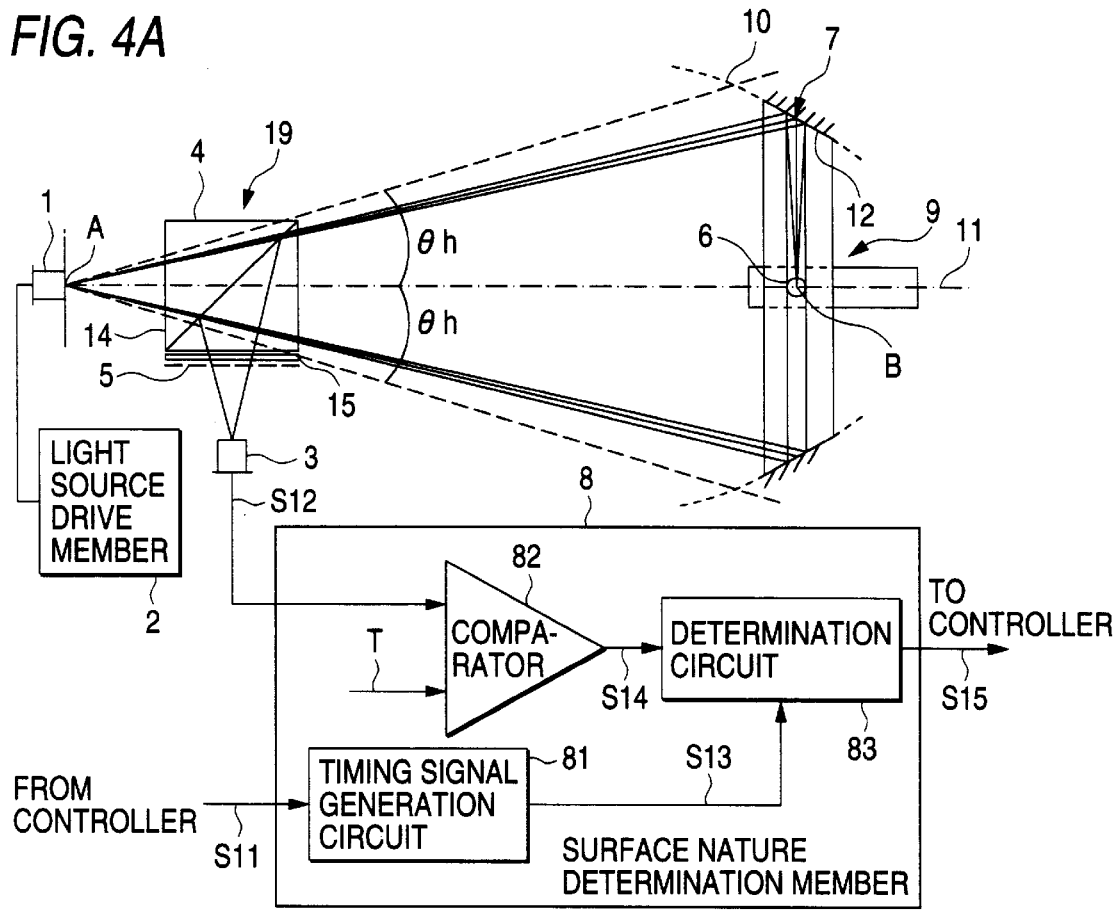
FIGS. 4A and 4B diagrammatic representations of the overall structure of spherical surface inspection equipment according to a first embodiment of the present invention.
Figure 4B:
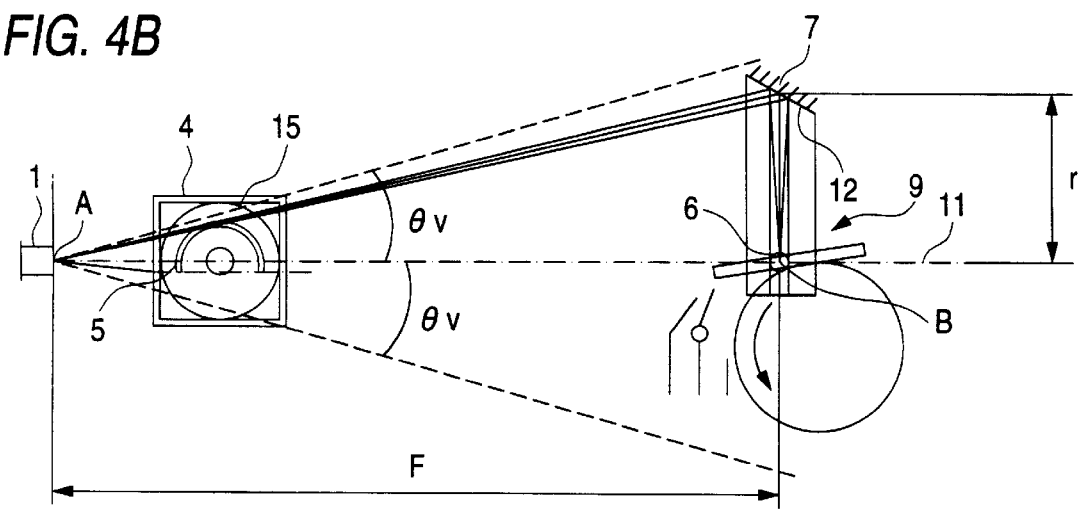
Figure 6A:
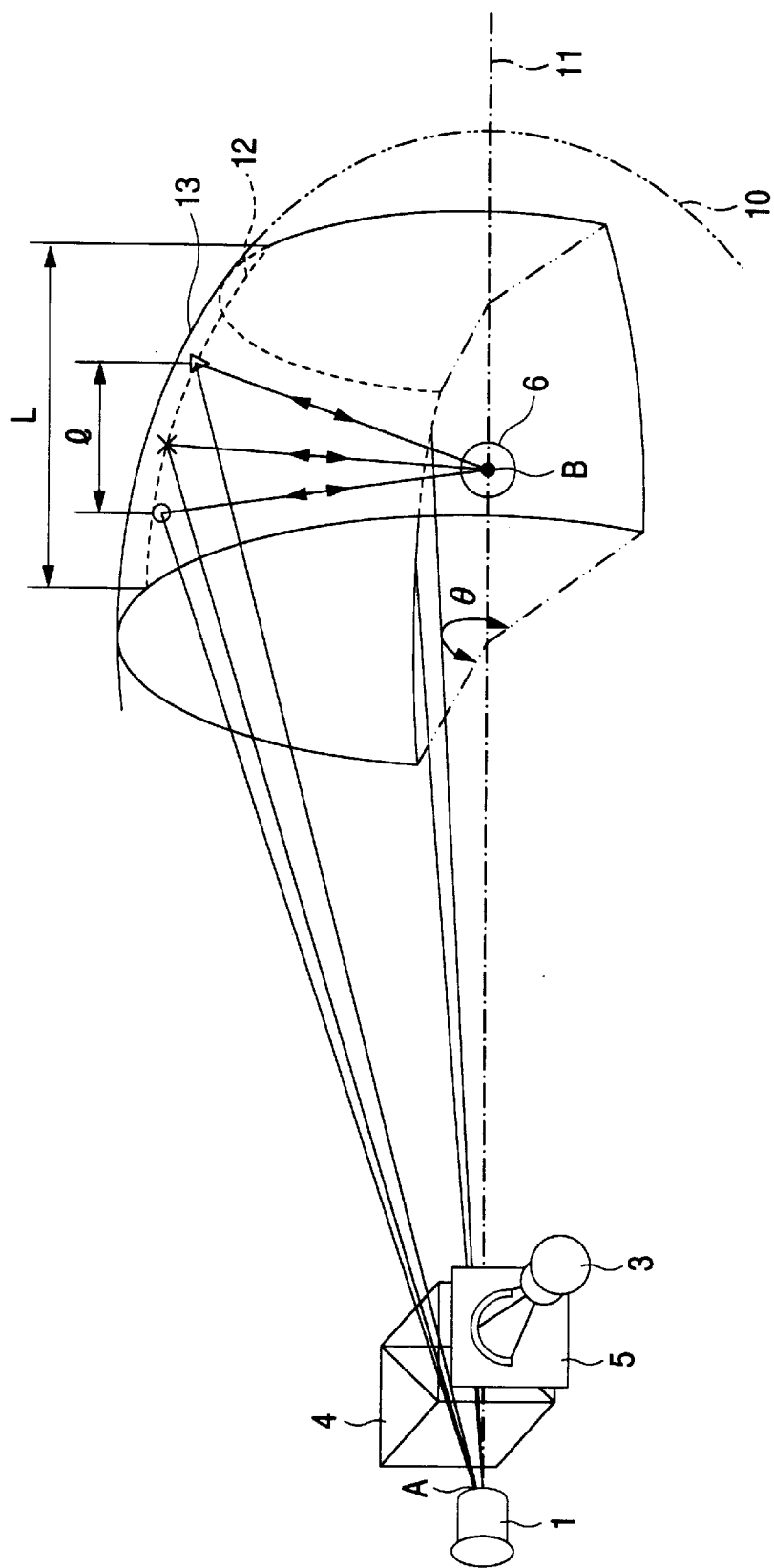
FIG. 6A and 6B are diagrammatic representations for explaining a predetermined inner surface area on an elliptical mirror which forms a deflecting member of the spherical surface inspection equipment illustrated in FIGS. 4A and 4B.
Figure 6B:
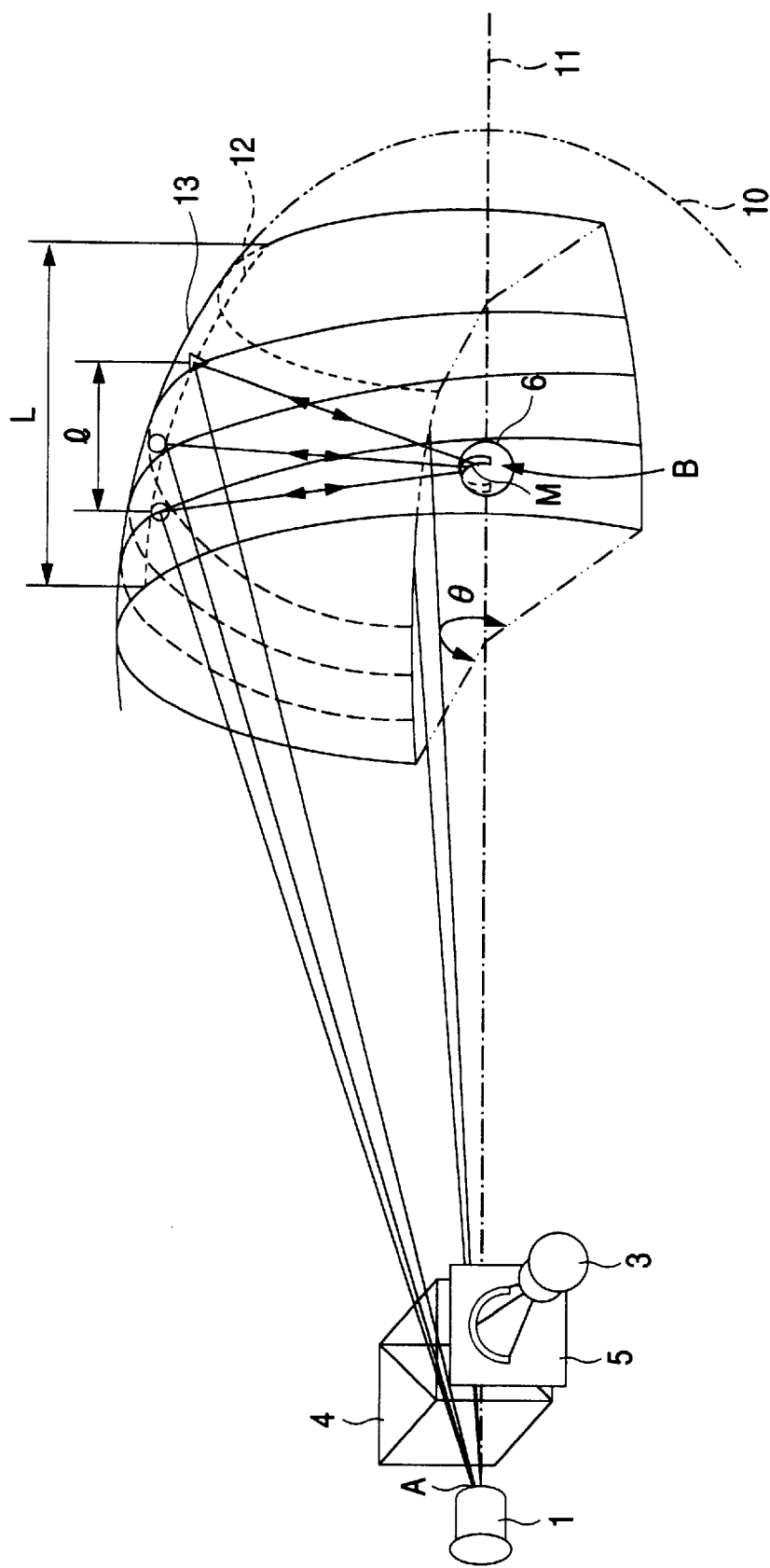
Figure 7:
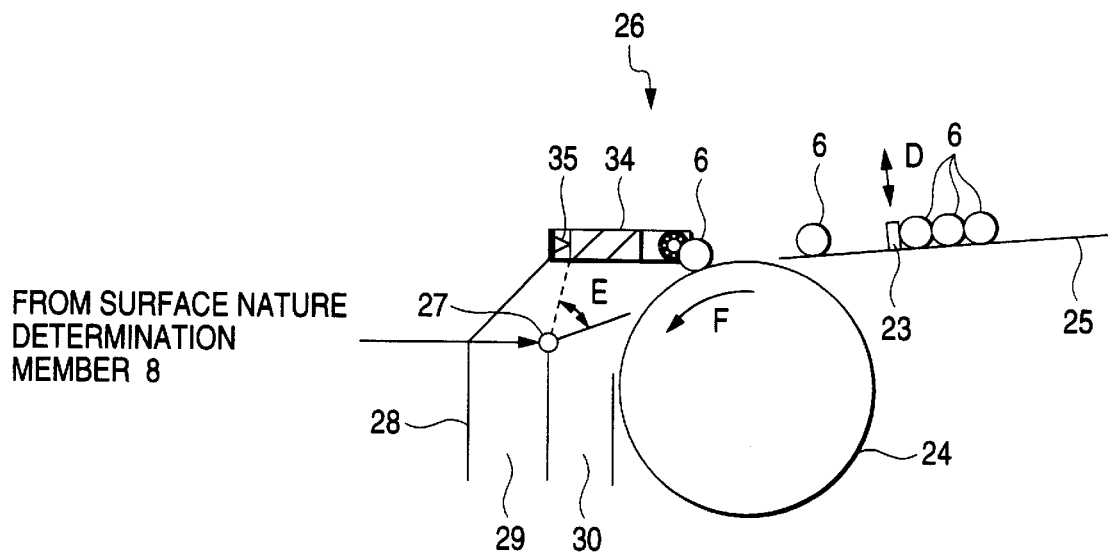
FIG. 7 is a detailed diagrammatic representation of a sphere inspection section of the spherical surface inspection equipment illustrated in FIGS. 4A and 4B.
Figure 11:
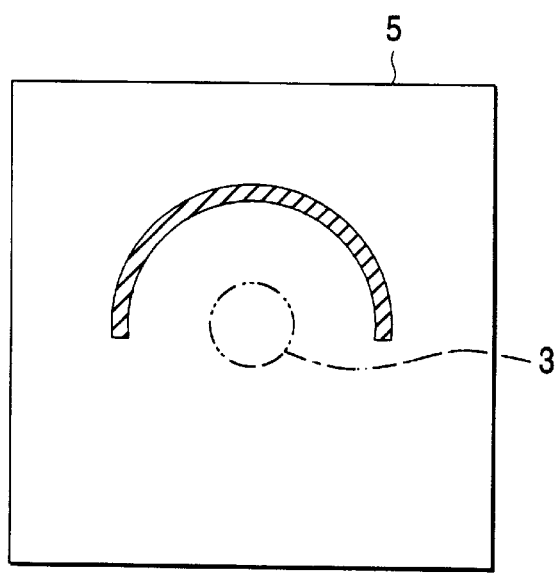
FIG. 11 is a schematic representation illustrating the layout relationship between a slit and a light detecting element of the spherical surface inspection equipment illustrated in FIGS. 4A and 4B.

FIGS. 4A and 4B are diagrammatic representations of the overall structure of spherical surface inspection equipment according to a first embodiment of the present invention; FIG. 5 is a timing chart illustrating signals input to and output from a surface nature determination member of the spherical surface inspection equipment illustrated in FIGS. 4A and 4B; FIG. 6 is a diagrammatic perspective view for explaining a predetermined region on the inner surface of an elliptical mirror which forms a deflecting member of the spherical surface inspection equipment illustrated in FIGS. 4A and 4B; FIG. 7 is a detailed diagrammatic representation of a sphere inspection section of the spherical surface inspection equipment illustrated in FIGS. 4A and 4B; and FIG. 11 is a schematic representation illustrating the layout relationship between a slit and a light detecting element of the spherical surface inspection equipment illustrated in FIGS. 4A and 4B.

As illustrated in FIGS. 4A and 4B, the spherical surface inspection equipment is provided with a laser diode (a point of light source having a light exit point measuring several micrometers) which emits a laser beam having a single wavelength of, e.g., 780 nm; and a light source drive member 2 which outputs a drive signal to the laser diode 1. The laser diode 1 is positioned such that the exit point of the laser diode is in line with a first focal point A of an ellipse 10 which also has a second focal point B, and that the optical axis (or the center axis) of an outgoing luminous flux is brought in alignment with a major axis 11.

The outgoing luminous flux emitted at specific angle of spread from the laser diode 1 via a beam splitter 4 is guided to an article to be inspected 6; i.e., a steel ball, in a given position by a deflecting member 7. The luminous flux reflected from the steel ball 6 is guided to a light detecting element 3 via the beam splitter 4 and a slit 5. The specific angle of spread used herein refers to an angular range which provides effective brightness capable of being used in examination.

Specifically, the deflecting member 7 is comprised of an elliptical mirror. In the elliptical mirror, a portion of a curved surface obtained by rotating around the major axis 11 the ellipse 10 having the first and second focal points A and B; namely, a predetermined inner-surface region 12, is used as a mirror surface. More specifically, as illustrated in FIG. 6A, the predetermined inner-surface region 12 has a widthwise area L larger than a widthwise area Q which corresponds to the light that finally arrives at the light detecting element 3 after having passed through the slit 5. In short, as illustrated in FIG. 6B, the predetermined inner-surface region 12 is formed into a mirror surface area having an angle θ of at least 180 degrees or, more preferably, 200 degrees in the drawing in such a way that the luminous flux reflected from the deflecting member 7 incidents on an area including a specific meridian M having a required minimum width on the upper surface of the steel ball 6.

The beam splitter 4 is made up of a half mirror which permits passage of the luminous flux emitted from the laser diode 1 and supplies the luminous flux to the light detecting element 3 through the slit 5 by reflecting the luminous flux reflected from the deflecting member 7. The slit 5 has a semi-annular window and is positioned in front of the light detecting element 3. A filter 15 is interposed between the beam splitter 4 and the slit 5 so as to selectively permit passage of the reflected luminous flux having a predetermined wavelength.

A method of determining the shape and size of the elliptical mirror will be described hereinafter.

As is commonly known, the light intensity distribution of the luminous flux emitted from the laser diode 1 in its cross-sectional direction perpendicular to the center axis of the luminous flux takes a Gaussian distribution in which the light intensity is maximum at the center of the luminous flux and becomes smaller toward the periphery of the same. Points having the same light intensity are distributed in the form of an elliptically curved pattern over the plane perpendicular to the optical axis. If the laser diode I is positioned in such a way that the major axis of the elliptically curved pattern corresponding to a specific light intensity is brought in alignment with a horizontal direction, the angle at the focal point A formed with respect to the predetermined inner-surface region 12 becomes smaller than an angle θv (illustrated in FIG. 4B) formed in the direction of a minor axis of the elliptically curved pattern of light intensity. With this arrangement, an angle θh (illustrated in FIG. 4A) in the direction of the major axis of the elliptically curved pattern of light intensity becomes sufficiently larger than the angle formed at the focal point A, so that the predetermined inner-surface region 12 is included in the area of the outgoing luminous flux. More specifically, provided that the focal point B is contained by the ellipse 10, that the radius of a circular arc which is an intersection between the plane perpendicular to the major axis 11 of the ellipse 10 and the predetermined inner-surface region 12 is "r," and that the distance between the focal points A and B is taken as F, the ellipse 10 is selected so as to satisfy Equation (1) provided below.

$$r/F < \tan \theta v \tag{1}$$

If the ellipse is represented by Equation (2) given below, the radius "r" and the distance F will be represented by Equations (3) and (4).

$$x^2/a^2 + y^2/b^2 = 1 \tag{2}$$

$$F = 2\sqrt{a^2 - b^2} = 2a\sqrt{1 - K^2} \tag{3}$$

$$r = b^2/a = Kb \tag{4}$$

where K is a parameter, and K=b/a.

Equation (5) given below is obtained from Equations (1), (3), and (4). It is also possible to select the ellipse 10 so as to satisfy the parameter K obtained by substituting the angle θv formed with respect to the minor axis into Equation (5).

$$K < \sqrt{2 \tan \theta v \left( \sqrt{\tan^2 \theta v + 1} - \tan \theta v \right)} \tag{5}$$

As a result of selection of angle θv of spread of the outgoing luminous flux and the parameter K so as to satisfy the previous equations, a part of the light focused on the first focal point A incidents on the predetermined inner surface area and is focused on the second focal point B without modification of the distribution of brightness.

In practice, first, a decision is made as to the extent to which a reduction in the light intensity distribution is allowed. The angle θv in the minor axis is determined according to the thus-determined allowable extent of reduction. Subsequently, the size of each element of the optical system is determined on the basis of the angle θv. For example, in the first embodiment, it is acknowledged that the reduction in the light intensity distribution up to 60% of the light intensity at the center of the luminous flux (or the maximum light intensity) can be permitted. The angle θv corresponding to this allowable extent of reduction, is 9 degrees. Therefore, the parameter K becomes smaller than 0.52. Provided that K=0.5 and a required radius "r"=100 mm, b=r/K=200 mm and a=b/K=400 mm are obtained. Although the previous embodiment has been described with reference to the case where the laser diode 1 is positioned in such a way that the major axis of the elliptically-curved pattern of light intensity is brought into alignment with a horizontal direction, the laser diode 1 can be positioned at an arbitrary angle with respect to the axis between the focal point A and the focal point B.

The light detecting element 3 is made up of; e.g., a photodiode which detects the luminous energy obtained through the previously-described optical path and converts the thus-detected luminous energy into an electrical signal having to a corresponding level by member of photoelectric conversion. As illustrated in FIG. 11, of the luminous flux reflected from the beam splitter 4, only the light that has passed through a semi-annular window of the slit 5 (a hatched portion in FIG. 11) enters and is photoelectrically converted by the light detecting element 3. The light detecting element 3 outputs a PD signal 12 which represents the detected luminous energy.

The PD signal 12 output from the light detecting element 3 is input to the surface nature determination member 8. The surface nature determination member 8 determines the nature of the surface of the steel ball 6 on the basis of the level of the PD signal 12 received from the light detecting element 3. More specifically, the surface nature determination member 8 has a comparator 82. This comparator 82 compares the level of the PD signal S12 with the level of a reference signal T and outputs an imperfection detection signal S14 which represents the result of such comparison. The imperfection detection signal S14 is output from the comparator 82 to a determination circuit 83. The determination circuit 83 determines whether or not there are imperfections, such as flaws, in the surface of the steel ball 6 on the basis of the imperfection detection signal S14, and outputs a determination signal S15 which represents the result of determination to a controller (not shown). The determination operation of the determination circuit 83 is controlled by a reset pulse signal S13 output from a timing signal generation circuit 81. This timing signal generation circuit 81 generates and outputs the reset pulse signal S13 on the basis of an instruction signal S11 received from the controller.

As illustrated in FIG. 5, in the surface nature determination member 8, the high-level instruction signal S11 which instructs initiation of the determination operation is output to the timing signal generation circuit 81 from the controller. Upon receipt of the high-level instruction signal S11, the timing signal generation circuit 81 outputs the reset pulse signal S13 to reset the determination signal S15 retained in the determination circuit 83.

The determination circuit 83 resets the determination signal S15 to a low level in response to the reset pulse signal S13 and monitors the imperfection detection signal S14 output from the comparator 82.

In contrast, the comparator 82 compares the level of a the PD signal S12 of the light detecting element 3 with the level of the reference signal T and outputs the imperfection detection signal S14 that represents the result of such comparison, to the determination circuit 83. For instance, if there are imperfections in the surface of the steel ball 6, the level of the PD signal S12 received from the light detecting element 3 becomes smaller than the level of the reference signal T at a point in time K in the drawing, and the imperfection detection signal 514 that represents the presence of imperfections is output. In response to the imperfection detection signal S14, the determination circuit 83 outputs the high-level determination signal S15, and the level of the determination signal S15 is retained until the next reset pulse signal S23 is input to the determination circuit 93.

As illustrated in FIGS. 4A and 4B, a sphere inspection section 9 feeds the steel ball 6 to the previously described predetermined location. The sphere inspections section 9 feeds the steel ball 6 to the predetermined location in such a way that the center of the steel ball 6 is placed in the second focal point B and rotates the thus-positioned steel ball 6. Further, the sphere inspection section 9 screens the steel ball 6 according to the nature of the surface thereof.

As illustrated in FIG. 7, the sphere inspection section 9 is comprised of a stopper 23 which moves in the direction designated by arrow D so as to stop the steel balls 6, a guide member 25 which guides the steel ball 6 to a driver roller 24 (which rotates in the direction designated by arrow F), a sphere driver member 26 for rotating the steel ball 6 while it is retained by the driver roller 24, and a selection member 28 for selecting a non-defective ball from a defective ball by pivoting a hinge 27 in the direction designated by arrow E according to the determination result represented by the determination signal S15 received from the surface nature determination member 8. More specifically, in the sphere inspection section 9, the steel bell 6 is conveyed to the driver roller 24 along the guide member 25 as a result of upward movement of the stopper 23. The steel ball 6 is rotated by the sphere driver member 26, and the surface nature determination member 8 determines the nature of the overall surface of the steel ball 6. According to the result of such determination made by the surface nature determination member 8, the hinge 27 is pivoted in the direction designated by arrow E. The thus-examined sphere is stored in either a non-defective storage section 29 or a defective storage section 30.

Figure 8:
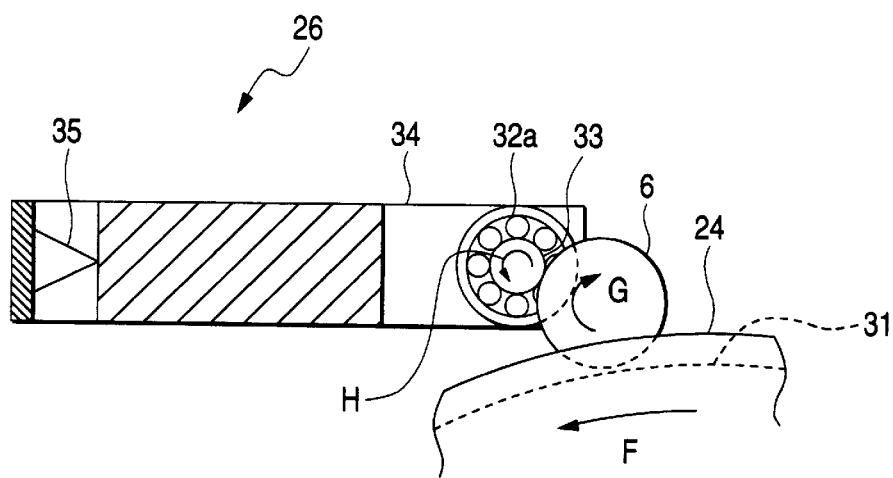
FIG. 8 is a detailed front view of a sphere drive member.
Figure 9:
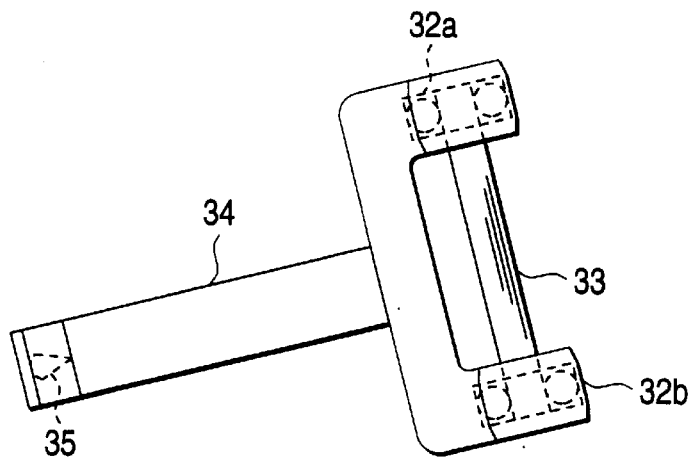
FIG. 9 is a detailed plan view of the sphere drive member.
Figure 10:
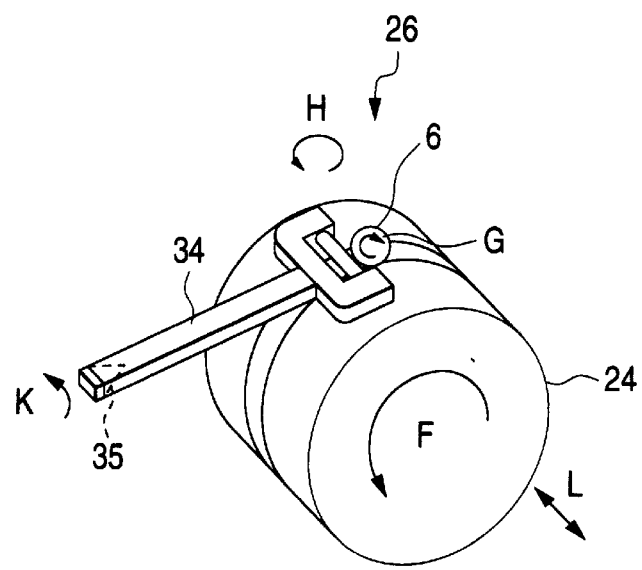
FIG. 10 is a perspective view of the sphere drive member.

With reference to FIGS. 8 through 10, the detailed structure of the sphere drive member 26 will be described. FIG. 8 is a front view illustrating the details of the sphere drive member; FIG. 9 is a plan view illustrating the details of the sphere driver member; and FIG. 10 is a perspective view of the sphere drive member.

As illustrated in FIGS. 8 through 10, the sphere drive member 26 is comprised of the previously-described drive roller 24 which has a V-shaped groove 31 formed therein to retain the steel ball 6 with a clearance fit and is rotated in the direction designated by arrow F via an unillustrated drive motor, a rod-shaped support roller 33 having both ends thereof rotatively supported by a pair of shaft bearings 32a and 32b, an arm section 34 which houses the bearings 32a and 32b, and a pivot 35 provided on the base end of the arm 34.

In the sphere drive member 26, if the drive roller 24 rotates in the direction designated by arrow F at the time of examination of the steel ball 6, the steel ball 6 rotates in the direction designated by arrow G by a frictional force developed between the steel ball 6 and the drive roller 24. The support roller 33 supports the steel ball 6 while rotating in the direction designated by arrow H. As a result, since the steel ball 6 rotates while its center is positioned at the second focal point B, all the light reflected from the deflecting member 7 incidents on the steel ball 6 at right angles, thereby scanning the overall surface of the steel ball 6 and examining the nature of the surface. After the inspection of the surface nature of the steel ball 6 has been completed, the pivot 35 pivots in the direction designated by arrow K. The steel ball 6 is detached from the drive roller 24 and is sent to the selection member 28. The drive roller 24 is movable along the line (in the direction designated by arrow L) between the position in which the center of the steel ball 6 is to be retained (i.e., the second focal point B) and the center of rotation of the drive roller 24. Consequently, it is possible to examine the surface nature of the differently-sized steel balls 6. Further, the pivot 35 of the sphere drive member 26 retains the steel ball 6 in the drive roller 24 or removes it from the same by member of the pivot 35, It goes without saying that a movable stage or other mechanism may be used in lieu of the pivot 35 to retain the steel ball 6 in the drive roller 24 or removes it from the same.

As illustrated in FIGS. 4A and 4B, in the spherical surface inspection equipment having the foregoing structure, an outgoing luminous flux emitted from the laser diode 1 whose luminous energy is controlled by the light source drive member 2, travels to the deflecting member 7 after having passed through the beam splitter 4. The luminous flux is reflected by the deflecting member 7. All the thus-reflected luminous flux simultaneously incidents at right angles on the surface of the steel ball 6 retained in the second focal point B toward the center of the steel ball 6, more specifically, on at least an area to be examined defined between the poles of the steel ball 6 in line with its axis of rotation (i.e., a substantially semi-circumferential strip-shaped area).

As described above, all the light is arranged to simultaneously incident on the steel ball 6 toward its center, and hence the reliability of selection of a non-defective ball from a defective ball carried out by use of the light reflected from the steel ball 6, which will be described later, is enhanced. The incoming light is guided to the steel ball by combination of a point source of light and an elliptical mirror without use of means which causes the incoming light to scan by use of a movable section, thereby resulting in stable incoming light.

The luminous flux that has incidented on the steel ball 6 at right angles is reflected from the steel ball 6, and the light reflected from the flaw- or stain-free area of the surface reversely travels along the path of the incoming light. The reflected light travels back again to the beam splitter 4 via the deflecting member 7, and the thus-returned luminous flux is reflected in the direction at right angles by the beam splitter 4. The luminous flux thus reflected at right angles by the beam splitter 4 is selected by the slit 5, and only the light that has passed through the window of the slit 5 enters the light detecting element 3. The light received by the light detecting element 3 is photoelectrically converted into the PD signal S12, and this PD signal S12 is output to the surface nature determination member 8. The surface nature determination member 8 determines the presence or absence of imperfections in the steel ball 6 according to the PD signal S12. The selection member 28 of the sphere inspection section 9 selects a non-defective steel ball 6 from a defective steel ball 6 according to the determination signal S15 that represents the result of such determination.

As illustrated in FIG. 11, of the luminous flux reflected from the beam splitter 4, only the light that has passed through the window of the semi-annular window of the slit 5 (hatched in FIG. 11) enters and is then photoelectrically converted by the light detecting element 3. If there are imperfections, such as flaws or stains, in the surface of the sphere inspection section 6, the light reflected from the flawed or stained area of the surface becomes scattered, thereby forming a pattern of high contrast corresponding to the flaws or stains on the surface of the window of the slit 5. For this reason, the luminous energy that has passed through the slit 5 changes. The light detecting element 3 detects such variations in the luminous energy, and the surface nature determination member 8 determines abnormalities in the steel ball 6 according to the result of such detection.

If the size of the steel ball 6 is changed, it is desirable to change the lower limit of the size of imperfections to be detected according to the size of the steel ball 6. However, the steel ball 6 is retained such that its center matches the second focal point B of the ellipse 10 in the present embodiment, and hence the incoming luminous flux is collected on the steel ball 6 toward its center. As a result, a constant solid angle is ensured regardless of the size of the steel ball 6, which in turn enables prevention of much as possible of the inconvenience of replacing components when the size of the steel ball 6 varies. Further, it is possible to examine the steel ball 6 while the optical axis of the incoming luminous flux is held stable.

The overall surface of the steel ball 6 is scanned by the light by rotating the steel ball 6 around a given axis while it is retained at the second focal point B of the ellipse 10, which in turn eliminates oblique rotation of the steel ball 6. Eventually, it becomes unnecessary to use a conventional control roller and to use a tilting mechanism which may cause errors in the rotating speed. As a result, it is possible to examine a ball having a small diameter with high accuracy.

Further, of the luminous flux reflected from the beam splitter 4, only the light that has passed through the semi-annular window of the slit 5 enters the light detecting element 3, whereby the width of the light that has entered the light detecting element 3 is limited in the radial width of the window of the slit 5. As a result, the influence of a reduction in the brightness caused by flaws can be relatively increased. In other words, the sensitivity of detection of flaws can be improved, and the accuracy of examination can be improved to a much greater extent. The sensitivity of light detection can be slightly increased by a combination of several light detection elements 3.

(SECOND EMBODIMENT)

Figure 12A:
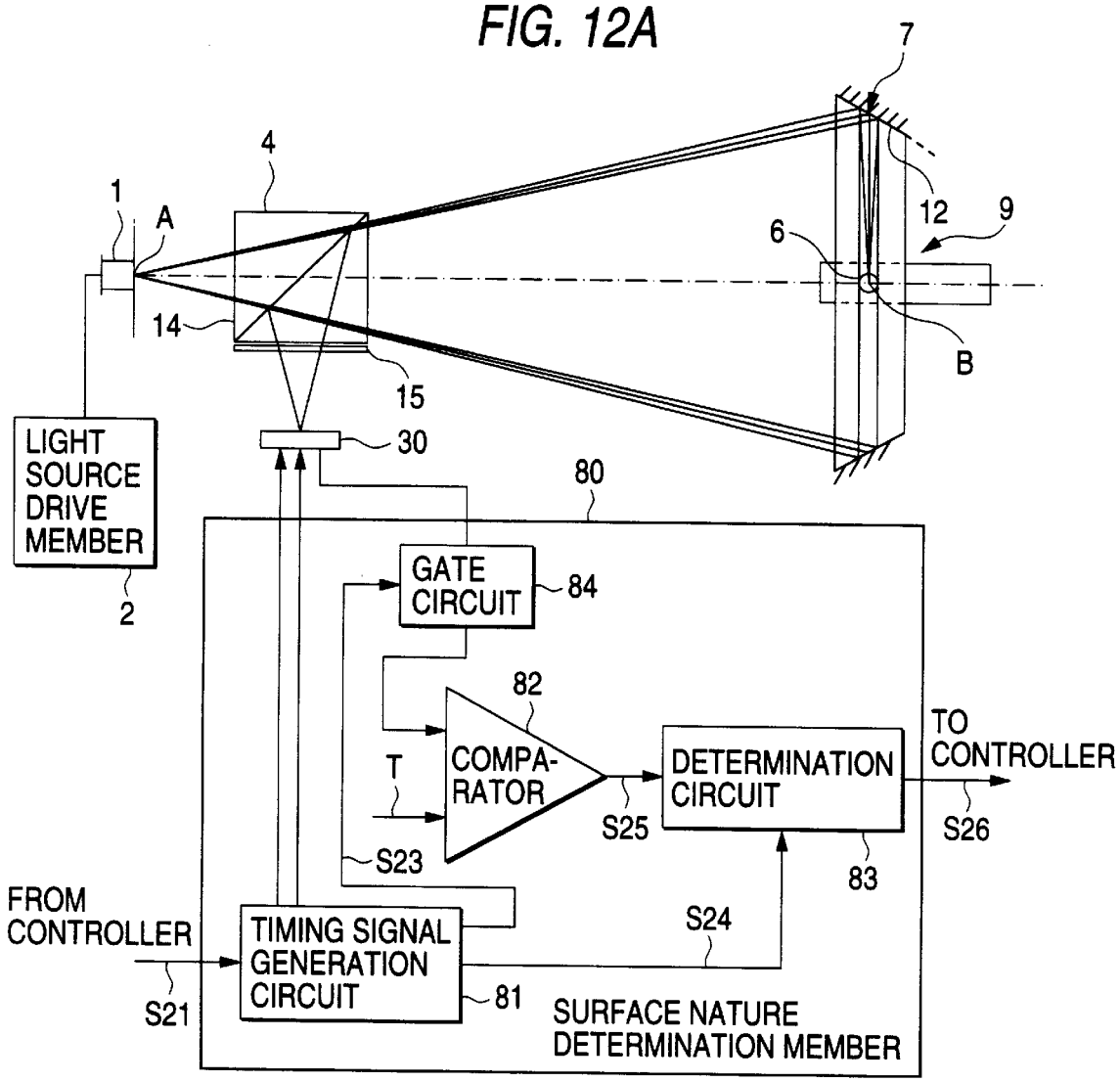
FIGS. 12A and 12B are diagrammatic representations of the overall structure of spherical surface inspection equipment according to a second embodiment of the present invention.
Figure 12B:
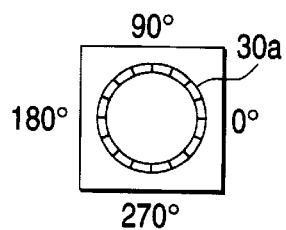
Figure 13:
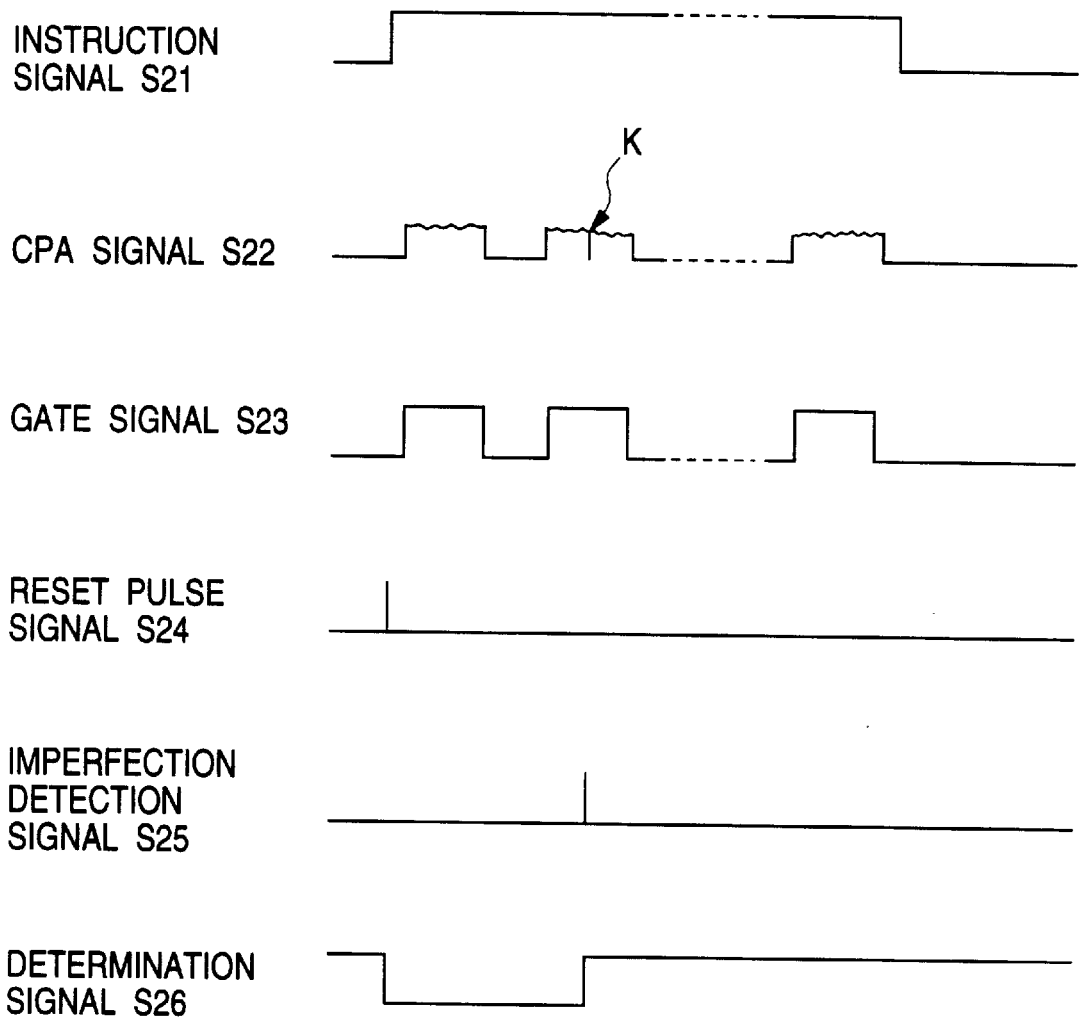
FIG. 13 is a timing chart illustrating signals input to and output from a surface nature determination member of the spherical surface inspection equipment illustrated in FIGS. 12A and 12B.

With reference to FIGS. 12A and 12B through FIGS. 14A to 14D, a second embodiment of the present invention will be described. FIGS. 12A and 12B are schematic representations of the overall structure of spherical surface inspection equipment according to the second embodiment. FIG. 13 is a timing chart illustrating signals input to and output from a surface nature determination member of the spherical surface inspection equipment illustrated in FIGS. 12A and 12B. FIGS. 14A to 14D are signal waveforms representing variations in the level of each of the principal signals illustrated in FIG. 13.

The second embodiment is characterized by replacement of the slit 5 and the light receiving element 3 used in the first embodiment with a circular photodiode array element (hereinafter referred to as a CPA). In the second embodiment, only the constituent elements of the second embodiment differing from those of the first embodiment will be described, and explanations for the constituent elements common to the first and second embodiments will be omitted here.

As illustrated in FIGS. 12A, the spherical surface inspection equipment is provided with a CPA 30 which detects the luminous energy of the light reflected from the steel ball 6 after having been reflected by the beam splitter 4 at right angles. As illustrated in FIG. 12B, the CPA 30 has a plurality of photodiodes 30*a* arrayed in a circular pattern on one surface of a substrate at uniform angular intervals. A light receiving area defined by the photodiodes 30*a* constitutes an annular area, and the radial width of the annular area is defined by a light-receiving width of each photodiode 30*a*. Therefore, the radial width of the light-receiving area defined by each photodiode 30*a* corresponds to the radial width of the window of the slit 5 of the first embodiment. More specifically, in addition to improvements in the detection accuracy resulting from limitation of the radial width of the incoming light, it is possible to further improve the inspection accuracy compared to that of the first embodiment by detection of the luminous energy in each position of the photodiodes 30*a*.

Each photodiode 30*a* detects the luminous energy of the received light and photoelectrically converts the thus-detected luminous energy into a CPA signal S22 having a corresponding level. The CPA signals S22 received from the photodiodes 30*a* are output in time sequence. Since the light-receiving area defined by each photodiode 30*a* is annular, the CPA signal S22 is comprised of an effective signal output from the photodiodes 30*a* substantially positioned in the semi-annular area (within a predetermined angular range) corresponding to the window of the slit 5 of the first embodiment, and an effective noise signal output from the photodiodes 30*a* positioned in the other area.

The CPA signal S22 output from the CPA 30 is delivered to the surface nature determination member 80, and this surface nature determination member 80 determines the surface nature of the steel ball 6 according to the level of the CPA signal S22. The surface nature determination member 80 is provided with a gate circuit 84 for extracting an effective signal included in the CPA signal S22. This gate circuit 84 permits passage of effective signals output from the photodiodes 30*a* located in a given angular range according to a gate signal S23 received from the timing signal generation circuit 81, and interrupts passage of ineffective signals. The comparator 82 compares the level of the effective CPA signal S22 that has passed through the gate circuit 84 and a level T of the reference signal T, and outputs the result of such comparison in the form of an imperfection detection signal S25. The thus-output imperfection detection signal S25 is delivered to the determination circuit 83, and this determination circuit 83 determines whether or not there are imperfections such as flaws in the surface of the steel ball 6 according to the imperfection detection signal S25. A determination signal S26 representing the result of such determination is output to the controller (not shown). The determination operation of the determination circuit 83 is controlled by a reset pulse signal S24 output from the timing signal generation circuit 81. The timing signal generation circuit 81 generates and outputs the gate signal S23 and the reset pulse signal S24 according to an instruction signal S21 received from the controller.

First, as illustrated in FIG. 13, the high-level instruction signal S21 which instructs initiation of a determination operation is supplied to the timing signal generation circuit 81 of the surface nature determination member 80 from the controller. Upon receipt of the high-level instruction signal S21, the timing signal generation circuit 81 outputs the reset pulse signal S24 to reset the determination signal S26 retained in the determination circuit 83, as well as outputting the gate signal S23 to extract an effective signal included in the PD signal S22.

The determination circuit 83 resets the determination signal S26 to a low level according to the reset pulse signal S24 and monitors the imperfection detection signal S25 received from the comparator 92.

In contrast, as illustrated in FIGS. 13 and 14A to 14D, the gate circuit 84 permits passage of the CPA signal S22 during a period of time corresponding to the pulse width of the gate signal S23, i.e., an effective signal. As illustrated in FIG. 14C. the comparator 82 compares the level of the effective CPA signal S22 that has passed through the gate circuit 84 with the level of the reference signal T, and outputs the result of such comparison to the determination circuit 83 in the form of the imperfection detection signal S25. For example, if there are imperfections in the surface of the steel ball 6 at point in time X in FIGS. 13 and 14A to 14D, the level of the CPA signal S22 (at the point in time K in the drawings) of the CPA signal S22 of the CPA 30 becomes smaller than the level T of the reference signal T. As a result, the imperfection detection signal S25 illustrated in FIGS. 13 and 14D is output. As illustrated in FIG. 13, the determination circuit 83 outputs the determination signal S26 whose level id held in a high state in response to the imperfection detection signal S25, and the level of the determination signal S26 is retained until the next reset pulse signal S24 is input.

(THIRD EMBODIMENT)

With reference to FIG. 15, a third embodiment of the present invention will be described. FIG. 15 is a schematic representation of the principal elements of spherical surface inspection equipment according to the third embodiment.

The third embodiment is characterized by replacement of the laser diode constituting the point light source in the respective previous embodiments with a point light source which uses a laser light source.

Since light can be guided to the predetermined inner surface area at uniform brightness, a light source which produces a luminous flux having a circular cross section when viewed in a direction perpendicular to the optical axis is used as the point of light source.

As illustrated in FIG. 15, the point light source used in the present embodiment is specifically comprised of a laser light source 1a, a condensing lens 1b for focusing a laser beam emanated from the laser light source 1a, and a member 1c positioned in a focal point on which the flux of laser collected by the condensing lens 1b converges. The member 1c permits passage of the flux of laser collected by the condensing lens 1b while limiting its size to such an extent (e.g., ten micrometers) that the flux of the laser can be deemed to be a point source of light. It is possible to use the point light source having the foregoing structure in lieu of the laser diode used in the respective preceding embodiments. With this structure, the member 1c is positioned such that the center of the pinhole of the member 1c matches the focal point (the focal point A in the first embodiment) of the ellipse.

(FOURTH EMBODIMENT)

Next, with reference to FIGS. 16A to 16E and 17A and 17B, a fourth embodiment of the present invention will be described. FIGS. 16A to 16E are diagrammatic representations illustrating the characteristics of a luminous flux reflected from the surface of a ball to be inspected in spherical surface inspection equipment according to a fourth embodiment of the present invention. FIGS. 17A and 17B are diagrammatic representations illustrating the structure of a tilting mechanism of a laser diode employed in the spherical surface inspection equipment of the fourth embodiment. FIG. 17A is a plan view illustrating the structure of a mechanism for tilting a laser diode, and FIG. 17B is a side view illustrating the structure of the mechanism for tilting the laser diode.

In contrast to the preceding first and second embodiments, the fourth embodiment employs a laser diode which constitutes a point source of light and is positioned such that the optical axis of the luminous flux emitted from the laser diode makes a given angle with respect to the major axis of the ellipse of the deflecting member.

Figure 16A:
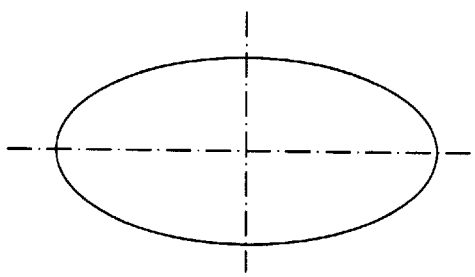
FIGS. 16A to 16E are diagrammatic representations illustrating the characteristics of a luminous flux reflected from the surface of a ball to be inspected in spherical surface inspection equipment according to a fourth embodiment of the present invention.
Figure 16B:
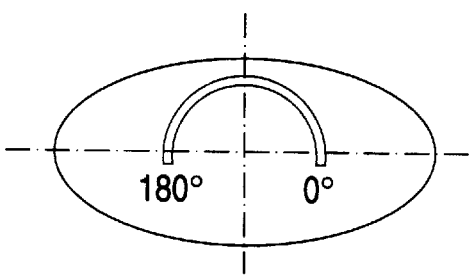
Figure 16C:
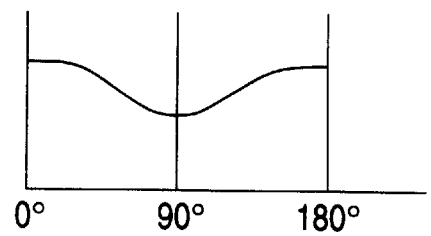
Figure 17A:
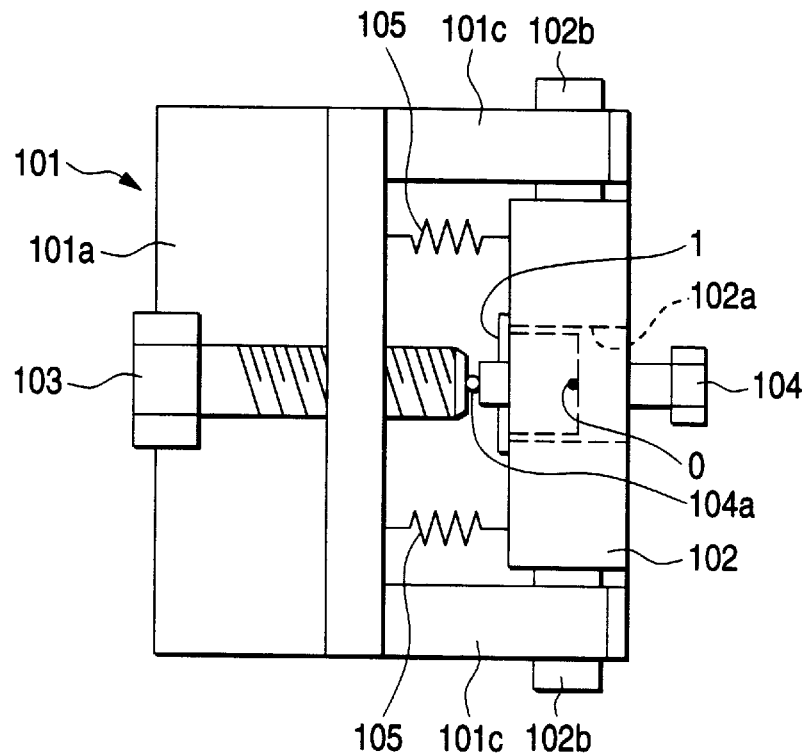
FIGS. 17A and 17B are diagrammatic representations illustrating the structure of a tilting mechanism of a laser diode employed in the spherical surface inspection equipment of the fourth embodiment.
Figure 17B:
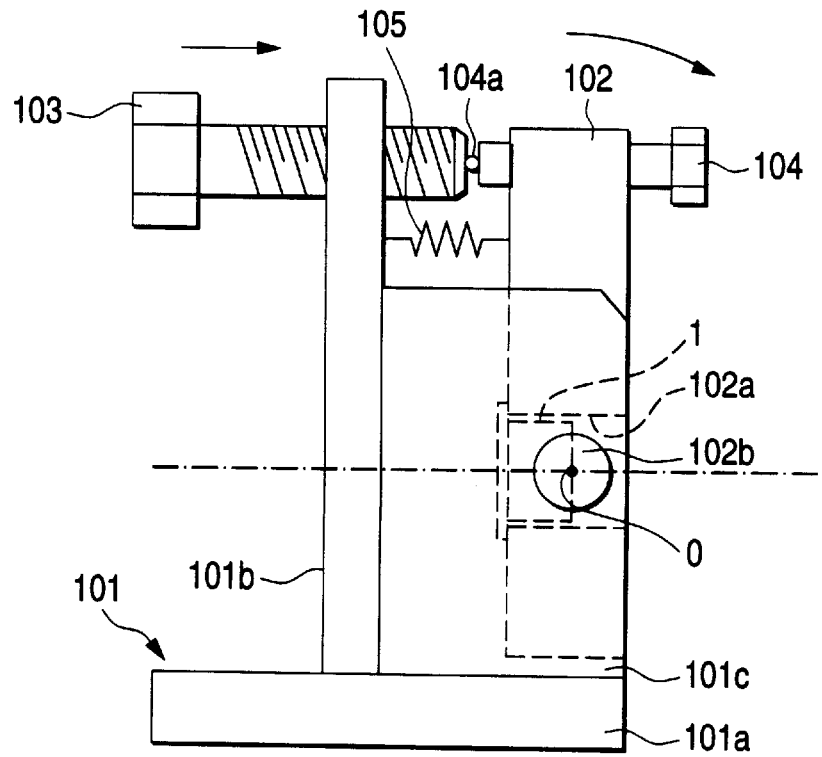

As illustrated in FIG. 16A, the luminous flux emitted from the laser diode has an elliptical cross section, and the light intensity of the luminous flux has two dimensional Gaussian distribution. In contrast to such a luminous flux emitted from the laser diode, as illustrated in FIG. 16C, there is a drop, in the vicinity 90 degrees within an angular range from 0 to 180 degrees, in the luminous energy of the light that has passed through a semi-annular slit illustrated in FIG. 16B formed so as to be concentric with a luminous flux emitted from the slit. As a result, the laser beam is emitted to the area of the sphere to be examined, at a different intensity according to an angle.

Figure 16D:
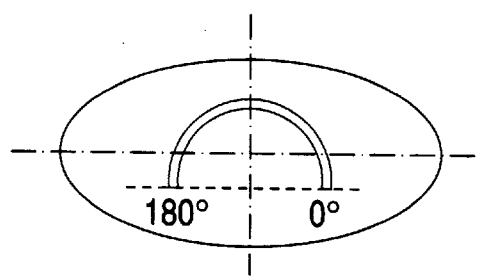
Figure 16E:
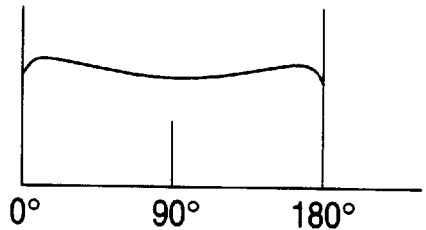

As illustrated in FIG. 16D to illuminate the area of the sphere to be examined at a uniform light intensity using a laser beam, the laser diode is positioned such that the center of the optical axis of the luminous flux emitted from the laser diode is offset from a semi-annular slit in the direction of its minor axis at the position where the luminous flux arrives at the slit. As illustrated in FIG. 16E, such an arrangement makes the luminous energy distribution of the luminous flux obtained after it has passed through the slit substantially uniform within an angular range of 0 to 180 degrees. Although the optical axis of the light emitted from the laser diode is brought into line with the major axis 11 of the ellipse in the first and second embodiments, the offset of the optical axis illustrated in FIG. 16D is accomplished by tilting the optical axis of the emitted light by a given angle corresponding to the degree of offset. Accordingly, it becomes possible to illuminate the area of the sphere to be examined using a laser beam at substantially uniform light intensity, which makes it possible to reliably eliminate faulty determination due to uneven illumination of the area to be examined. When compared with the structure of the spherical surface inspection equipment of the first and second embodiments provided that the same allowance of light intensity is ensured in both the first, second, and fourth embodiments, the present embodiment permits the major and minor axes (i.e., the distance between the focal points A and B) of the ellipse which defines the elliptical mirror to be set shorter than those of the first and second embodiments. Therefore, the spherical surface equipment can be made more compact, and its accuracy can be improved.

In consideration of the previous descriptions, an ellipse is obtained by Equation (1) or (5) while it is corrected taking into account the amount of eccentricity of the optical center at the position of the luminous energy detection member corresponding to the previously-described angle of inclination of the axis of the outgoing light.

Next, in reference to FIGS. 17A and 17B, an explanation will be given of the structure of the tilting mechanism for tilting the axis of the outgoing light emitted from the laser diode by a predetermined angle corresponding to the amount of eccentricity.

As illustrated in FIGS. 17A and 17B, the tilting mechanism is provided with a stand 101 for retaining the laser diode 1. The stand 101 is made up of a bottom plate 101a placed on a support surface, a front plate 101b standing upright on the bottom plate 101a, and a pair of side plates 101c which stand upright on the bottom plate 101a and forms a wall having a rectangular letter C-shaped cross section together with the front plate 101b.

The side plates 101c are disposed so as to be opposite to each other, and a rotary plate 102 is interposed between them. An opening 102a is formed in the rotary plate 102 so as to retain the laser diode 1 and to permit passage of light emitted from the laser diode 1. Further, the rotary plate 102 is provided with a pair of pivots 102b which are disposed in alignment with an axis which runs through exit point 0 of the laser diode 1 in parallel to the bottom plate 101a in a longitudinal direction thereof. The pivots 102b pass through and are supported by the corresponding side plates 101c so as to be rotatable around the axis. The rotary plate 102 rotates around the pivots 102b, and angle of rotation of the rotary plate 102 is adjusted according to a feed rate of a feed screw 103 fitted into the front plate 101b. The feed screw 103 projects from the front plate 101b to the rotary plate 102, and the front end of the feed screw 103 is in pressed contact with a front end 104a of a stopper 104 fixed to the rotary plate 102 by the return force of springs 105. Each of the springs 105 is fixed at one end thereof to the front plate 101a and at the other end thereof is fixed to the rotary plate 102.

At the outset, the tilting mechanism having the foregoing structure is placed on a predetermined support surface in such a way that the exit point 0 of the laser diode 1 comes into alignment with the focal point (the focal point A in the first embodiment) of the ellipse of the deflecting member, and that the optical axis of the outgoing luminous flux makes a predetermined initial angle with respect to the major axis of the ellipse of the deflecting member. Next, the tilting mechanism is inclined by a predetermined angle corresponding to the amount of eccentricity in order to illuminate the area of the steel ball to be examined at as uniform intensity as possible through use of a laser beam. During the adjustment of the tilting mechanism, the feed screw 103 is fed to the rotary plate 102. As the feed screw 103 is fed, the feed screw 103 pushes the front end 104a of the stopper 104 opposing the return force of the springs 105, whereby the rotary plate 102 is rotated about the pivots 102b by an angle corresponding to the feed rate of the feed screw 103. The rotary plate 102 is rotated according to the feed rate of the feed screw 103, and the optical axis of the luminous flux emitted from the laser diode 1 is tilted together with the rotation of the rotary plate 102 with respect to the major axis of the ellipse of the deflecting member. Intensity of illumination is measured at the position of a light-detecting element (the position of the light detecting element 3 in the first embodiment) every time the feed screw 103 is fed by a predetermined rate; namely, every time the optical axis of the outgoing luminous flux is inclined according to the feed rate. If it is confirmed as a result of such measurement of illumination that the area of the steel ball to be examined is illuminated at uniform intensity by the laser beam, the optical axis of the outgoing luminous flux has been tilted by the angle corresponding to the amount of eccentricity. The adjustment operation is now completed. It goes without saying that the inclination of the optical axis of the outgoing luminous flux involved in the fourth embodiment becomes unnecessary if there is used as the point of light source the laser employed in the third embodiment or another commercially available light source which produces the circular distribution of uniform intensity on a plane perpendicular to the optical axis by a combination of a laser diode, a micro-lens, and a correcting optical system.

(FIFTH EMBODIMENT)

Figure 18A:
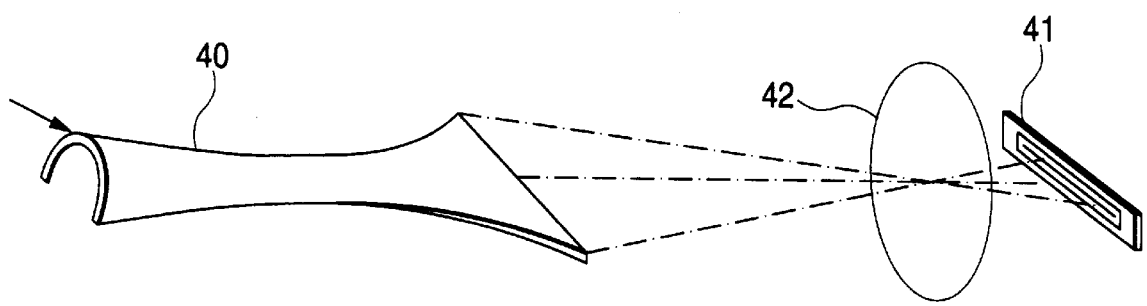
FIGS. 18A and 18B are diagrammatic representations illustrating the structure of a luminous energy detection member of spherical surface inspection equipment according to a fifth embodiment of the present invention.
Figure 18B:
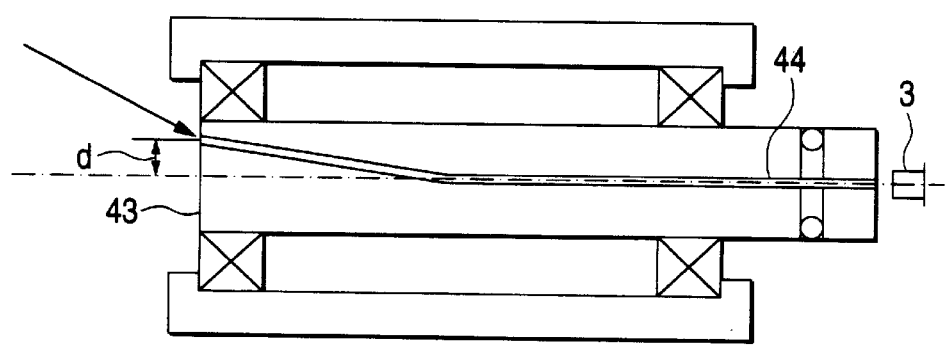

With reference to FIGS. 18A and 18B, spherical surface inspection equipment of a fifth embodiment of the present invention will be described. FIGS. 18A and 18B schematically illustrate the structure of the luminous energy detection member employed in the fifth embodiment of the spherical surface inspection equipment.

The fifth embodiment is characterized by exchanging the CPA employed in the second embodiment with luminous energy detection member made by a combination of an optical fiber and a linear image sensor less expensive than the CPA.

As illustrated in FIG. 18A, the luminous energy detection member employed in the fifth embodiment is comprised of a fiber bundle 40 consisting of a bundle of plurality of optical fibers. The fiber bundle 40 is at one end tied in a semi-annular pattern but is at the other end tied in a line. The fiber bundle 40 having such a construction receives at one end a semi-annular image (light reflected from the steel ball) and outputs from the other end an elongated strip-shaped image.

The image output from the other end of the fiber bundle 40 is focused by an optical lens 42 on an image pick-up surface of a linear image sensor 41. The linear image sensor 41 photoelectrically converts the image received from the other end of the fiber bundle 40 into an electrical signal. In short, the luminous energy of the light reflected from the steel ball is output in the form of an electrical signal, and this electrical signal is output in the same way as in the CPA.

If a blur is allowed to a certain extent, it is also possible for the linear image sensor 41 directly receive an image from the other end of the fiber bundle 40 without use of the optical lens 42 by arranging the linear image sensor 41 in the vicinity of the other end of the fiber bundle 40.

As illustrated in FIG. 18B, a fiber bundle 44 which consists of a bundle of a plurality of optical fibers and is inserted into a rotary shaft 43 of a spindle may be used as another detection member in lieu of the previous luminous energy detection member. One end of the fiber bundle 44 is exposed at one end of the rotary shaft 43 in an eccentric position with reference to the axis of the same, and the other end of the fiber bundle 44 is exposed at the other end of the rotary shaft 43 in line with the axis of the same.

The fiber bundle 44 inserted in the rotary shaft 43 of the spindle receives at one end light reflected from the steel ball and emits the light received from the other end in the axial direction of the rotary shaft 43 of the spindle. The light detection element 3 detects the luminous energy emitted from the other end of the fiber bundle 44. During the examination of the steel ball, the rotary shaft 43 of the spindle is rotated, and one end of the fiber bundle 44 moves along a circumference having a radius "d" around the axis of the rotary shaft 43. The surface of the steel ball is scanned as a result of movement of one end of the fiber bundle 44. A detection signal corresponding to the luminous energy obtained as a result of scanning of the fiber bundle 44 is output from the light detection element 3.

(SIXTH EMBODIMENT)

Figure 19A:
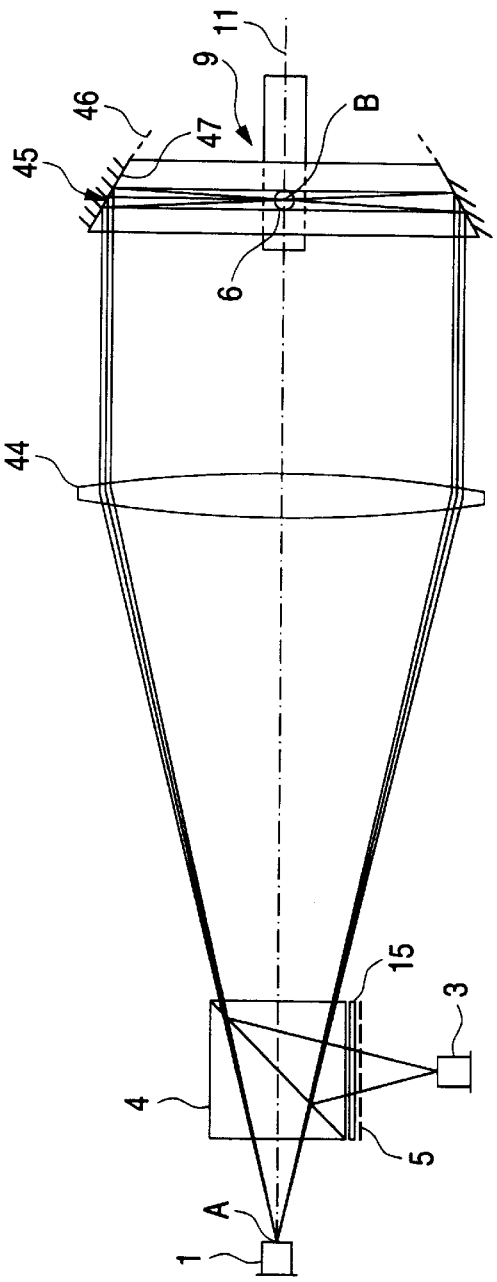
FIGS. 19A and 19B are diagrammatic representations illustrating the overall structure of spherical surface inspection equipment according to a sixth embodiment of the present invention.
Figure 19B:
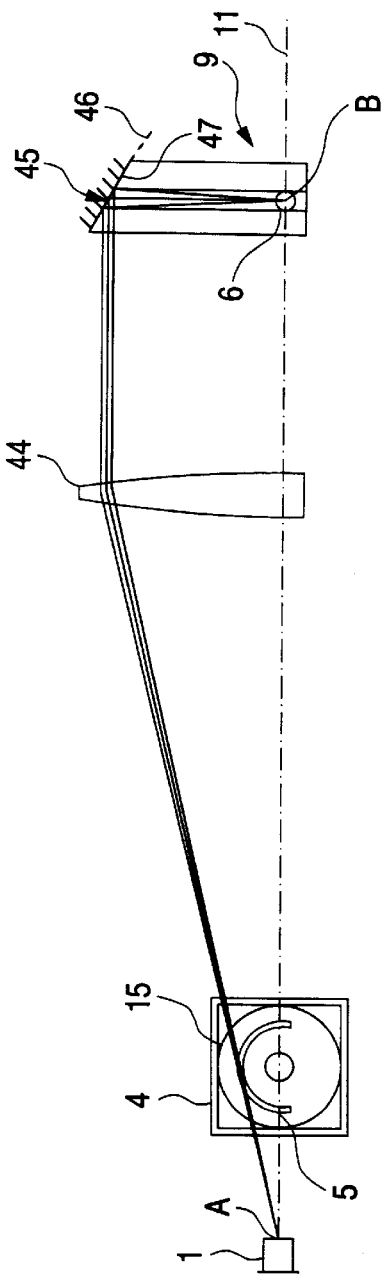

Next, with reference to FIGS. 19A and 19B, spherical surface inspection equipment of a sixth embodiment of the present invention will be described. FIGS. 19A and 19B schematically illustrate the overall structure of the spherical surface inspection equipment of the sixth embodiment. FIG. 19A is a plan view illustrating the configuration of the spherical surface inspection equipment of the sixth embodiment, and FIG. 19B is a side view illustrating the configuration of the spherical inspection equipment.

The sixth embodiment is characterized by exchanging the deflecting member 7 consisting of an elliptical mirror employed in the first and second embodiments with a combination of a collimator lens 44 and a parabolic mirror 45. As illustrated in FIGS. 19A and 19B, a luminous flux emitted from the laser diode 1 placed in the focal point A of the collimator lens 44 through the beam splitter 4 is collimated by the collimator lens 44 and then guided to the parabolic mirror 45. The distance between the collimator lens 44 and the parabolic mirror 45 can be freely set, which in turn enables realization of compact spherical surface inspection equipment and an improved degree of freedom of design.

The parabolic mirror 45 has as a mirror surface a predetermined area 47 within an inner surface of a parabolic surface which results from rotation of a parabola 46 around the major axis 11. The steel ball 6 is retained at the focal point B by the sphere inspection section 9 while the center of the steel ball 6 is aligned with the focal point B.

The collimated luminous flux that has exited from the collimator lens 44 is reflected from the parabolic mirror 45. The thus-reflected luminous flux incidents at right angles on the surface of the steel ball 6 retained in the focal point B toward the center of the steel ball 6, more specifically, on an area to be examined defined between the poles of the steel ball 6 in line with its axis of rotation.

The luminous flux that has thus incidented on the steel ball 6 is reflected by the steel ball 6. The light reflected from the flaw- or stain-free surface area reversely travels along the path of the incoming light. The reflected light travels back again to the beam splitter 4 via the parabolic mirror 45 and the collimator lens 44, and the thus-returned luminous flux is reflected in the direction at right angles by the beam splitter 4. The luminous flux thus reflected at right angles by the beam splitter 4 is selected by the slit 5, and only the light that has passed through the window of the slit enters the light detecting element 3. Then, the same operation as that carried out in the first embodiment is carried out, and the sphere inspection section 9 selects a non-defective steel ball 6 from a defective steel ball 6 according to the result of examination.

As has been described above, by virtue of the spherical surface inspection equipment of the present invention, the sphere-to-be-inspected drive member rotates the sphere around the predetermined axis that runs through the sphere while retaining it in a predetermined position. The light illumination member deflects the light emitted from the light source toward the center of the sphere along at least area to be examined which is defined between the poles of the sphere in line with the predetermined axis. The luminous energy detection member guides the light reflected from the area of the sphere to be examined along a predetermined optical path and detects the luminous energy of the thus-guided light. The surface nature determination member determines the nature of the examined surface area of the sphere according to the thus-detected luminous energy. As a result, constant solid angle of the incoming light with respect to the sphere is ensured. It becomes unnecessary to adjust the solid angle of the incoming light with respect to the sphere by exchange of components so as to change an optical system according to variations in the size of the sphere. This saves labor involved in preparation for measurement, and the sphere can be examined while the optical axis of the incoming light is held stable.

The entire surface of the sphere is scanned by rotation of the sphere around the predetermined axis while the sphere is retained in the predetermined location. As a result, it becomes unnecessary to obliquely rotate the, sphere, which in turn eliminates the need of a conventional control roller. Further, it becomes possible to eliminate the need of a skewing mechanism which may cause errors in the rotating speed, and the sphere can be examined while it rotates one time. Consequently, it is possible to provide inexpensive spherical surface inspection equipment capable of examining a small-sized sphere at a high speed with high accuracy, as well as of requiring easy operation and maintenance.

Moreover, the sphere does not need to be tilted, nor does it need to be scanned by light. Because, the incoming light simultaneously incidents on at least the area of the sphere through 180 degrees. Further, it is not necessary to ensure synchronization between the scanning of the area to be examined and the detection of the reflected light, which enables easy and reliable examination of the entire circumference of the sphere.

Several embodiments of the invention have now been described in detail. It is to be noted, however, that these descriptions of specific embodiments are merely illustrative of the principle underlying the inventive concept. It is contemplated that various modifications of the disclosed embodiments, as well as other embodiments of the invention will, without departing from the spirit and scope of the invention, be apparent to those who are versed in the art.

What is claimed is:

1. Spherical surface inspection equipment for optically examining the nature of the surface of a sphere comprising:

a light illumination member (1, 7) including;
      a point-source light (1) for emitting a luminous flux at predetermined angle of spread ($\theta v$) in a specific direction which is disposed in such a way that the exit point of the luminous flux matches a first focal point (A); and
      a curved-surface mirror (7) having a mirror surface defined by a predetermined inner surface area (12) which forms a part of a curved surface obtained by rotating a specific curve around a specific axis (11) containing said first focal point (A) and extended through at least 180 degrees around the axis;
      wherein said light illumination member (1, 7) is arranged such that the luminous flux emitted from said point-source light simultaneously enters an area including the predetermined inner surface area (12) of the curved-surface mirror (7), and that the light reflected from the curved-surface mirror is focused on a second focal point (B) contained in said specific axis (11);

sphere-to-be-examined driver (26) for retaining said sphere (6) such that its center is brought in alignment with the second focal point (B), and for rotating said sphere (6) about a rotational axis defined by straightly connecting the two poles on the sphere (6),
      wherein a specific meridian (M) extended through at least 180 degrees around the axis is defined on the surface of the sphere opposite to the predetermined inner surface of the curved-surface mirror by connecting said two poles along the surface of said sphere; and surface nature determination member (3, 8) for limiting said light reflected from said sphere (6) to only the light reflected from an area corresponding to a predetermined width containing said specific meridian; for detecting the thus-limited reflected light with at least one photodiode; and for determining the nature of the surface of the sphere according to the result of such detection.

2. The spherical surface inspection equipment as defined in claim 1, wherein the curved-surface mirror uses a part of a curved surface formed by rotating an ellipse around its major axis, and angle of spread ($\theta v$) of said outgoing luminous flux and K are selected so as to satisfy the following relationship, provided that the major axis is A, the minor axis is b, and K=b/a, $$K < \sqrt{2\tan\theta v(\sqrt{\tan^2\theta v + 1} - \tan\theta v)}.$$

3. The spherical surface inspection equipment as defined in claim 1, wherein at least one photodiode which measures so as to correspond to the predetermined width detects light in the surface nature determination member.

4. The spherical surface inspection equipment as defined in claim 1, wherein the optical axis of the point-source light is tilted at a predetermined angle with reference to the specific axis.

5. The spherical surface inspection equipment as defined in claim 1, wherein the light illumination member is provided with a curved-surface mirror formed as a result of rotation of a parabola, and a collimator lens for collimating the outgoing luminous flux focused on the first focal point into light parallel to the specific axis.

6. The spherical surface inspection equipment as defined in claim 1, wherein the point-source light is arranged to produce the luminous flux having a circular cross section when viewed in a direction perpendicular to the optical axis.

* * * * *